(12) United States Patent
Nguyen et al.

(10) Patent No.: US 12,283,868 B2
(45) Date of Patent: Apr. 22, 2025

(54) VIBRATION ACTUATOR FOR SHEAR WAVE ELASTOGRAPHY, SYSTEM AND METHOD

(71) Applicant: KONINKLIJKE PHILIPS N.V., Eindhoven (NL)

(72) Inventors: Man M Nguyen, Melrose, MA (US); Ramon Quido Erkamp, Swampscott, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 134 days.

(21) Appl. No.: 18/266,667

(22) PCT Filed: Dec. 14, 2021

(86) PCT No.: PCT/EP2021/085574
§ 371 (c)(1),
(2) Date: Jun. 12, 2023

(87) PCT Pub. No.: WO2022/128971
PCT Pub. Date: Jun. 23, 2022

(65) Prior Publication Data
US 2024/0055936 A1   Feb. 15, 2024

Related U.S. Application Data

(60) Provisional application No. 63/125,539, filed on Dec. 15, 2020.

(51) Int. Cl.
A61B 8/08 (2006.01)
A61B 8/00 (2006.01)
(Continued)

(52) U.S. Cl.
CPC ............. *H02K 7/063* (2013.01); *A61B 8/485* (2013.01); *G01N 29/043* (2013.01); *H02K 11/22* (2016.01); *A61B 8/4488* (2013.01)

(58) Field of Classification Search
CPC ............................. A61B 8/485; G01N 29/043
See application file for complete search history.

(56) References Cited

U.S. PATENT DOCUMENTS 4,084,445 A    4/1978 Erwin
4,793,196 A   12/1988 Davis et al.
(Continued)

OTHER PUBLICATIONS

International Search Report and Written Opinion for PCT/EP2021/085574; Mailing date: Mar. 29, 2022, 10 pages.
(Continued)

*Primary Examiner* — Colin T. Sakamoto

(57) ABSTRACT

A vibration actuator (10) for mechanically generating a shear wave comprises a plurality of n rotational vibrators (141, 142, 143), an accelerometer (16), and a controller (18). The plurality of n rotational vibrators enables generation of a vibration vector with desired directional behavior selected from a plurality of vibration vectors (34, 36, 38) of different directional behaviors. Each rotational vibrator comprises an independently controllable motor (20) having a drive shaft (22) and an eccentric disk (24). The accelerometer is arranged to detect a vibration vector generated by at least two of the plurality of n rotational vibrators. The controller selectively controls a first set of two rotational vibrators to rotate respective eccentric disks in a first coordinated manner to produce a first vibration vector, and a second set of two rotational vibrators to rotate respective eccentric disks in a second coordinated manner to produce a second vibration vector, with different respective directional behaviors.

20 Claims, 8 Drawing Sheets

(51) Int. Cl.
    *G01N 29/04*     (2006.01)
    *H02K 7/06*     (2006.01)
    *H02K 11/22*     (2016.01)

(56) References Cited

U.S. PATENT DOCUMENTS

| | | | |
|---|---|---|---|
| 10,709,423 B2 * | 7/2020 | Sakaguchi | G01S 7/52042 |
| 2007/0100240 A1 * | 5/2007 | Hiltawsky | A61B 8/485 |
| | | | 600/459 |
| 2014/0060958 A1 * | 3/2014 | Eick | G01V 1/153 |
| | | | 181/121 |
| 2016/0213350 A1 * | 7/2016 | Lee | A61B 8/4416 |
| 2016/0349143 A1 | 12/2016 | Aronstam | |

OTHER PUBLICATIONS

Neumann, W. et al., "A novel 3D-printed mechanical actuator using centrifugal force for magnetic resonance elastography", 9th Annual International Conference of the IEEE Engineering in Medicine and Biology Society (EMBC), 2017, pp. 3541-3544.

* cited by examiner

VIBRATION ACTUATOR FOR SHEAR WAVE ELASTOGRAPHY, SYSTEM AND METHOD

CROSS-REFERENCE TO PRIOR APPLICATIONS

This application is the U.S. National Phase application under 35 U.S.C. § 371 of International Application No. PCT/EP2021/085574, filed on Dec. 14, 2021, which claims the benefit of U.S. Provisional Patent Application No. 63/125,539, filed on Dec. 15, 2020. These applications are hereby incorporated by reference herein.

BACKGROUND

The present embodiments relate generally to vibration actuators and systems and more particularly, to a vibration actuator for shear wave elastography, system, and a method of mechanically generating a shear wave.

Viscoelastic properties of tissue are correlated to pathological processes such as cancer and inflammation. In addition, the viscoelastic properties of tissue can provide significant contrast between healthy and diseased tissues. This is why palpation can be used, for example, to detect tumors in breasts and thyroid of the human body.

One method for determining viscoelastic properties of tissues comprises diagnosis by palpation. Such a method however is limited to superficial and large structures with significant elastic contrast. In addition, diagnosis by palpation is subjective, as efficacy depends strongly on the skill of the person performing the diagnosis.

Besides palpation, ultrasound can be used to measure elastic properties of tissue. This is accomplished by inducing a mechanical perturbation that produced a mechanical wave (i.e., shear wave), and measuring the speed of this wave as it propagates through tissue. The wave speed is directly related to tissue stiffness, with a faster speed indicating stiffer tissue. This method works at deeper depths and is quantitative.

Shear wave elastography imaging is an existing feature on premium ultrasound imaging systems. With such ultrasound imaging systems, shear waves are generated with a special acoustic push pulse, and tracked using ultrasound imaging beams. The push pulse for shear wave generation has high power and extended duration, which undesirably creates special requirements on the imaging probe design and driving electronics. As a result, shear wave elastography is only available on a limited selection of ultrasound imaging probes on premium/high end platforms, such as Philips EPIQ™ and Philips iU22™, available from Koninklijke Philips N.V.

Shear waves can also be generated using a mechanical vibrator, avoiding the need for special requirements on probe design and driving electronics. This allows implementation of shear wave elastography on the larger family of ultrasound imaging platforms and probes that currently do not have this feature. However, there are a number of problems and disadvantages with known devices and methods, In one known example of a vibrator for an ultrasound imaging tool, a pair of flywheels are driven by a motor in opposing rotational paths so as to introduce a harmonic mechanical excitation to an object. In this regard, one flywheel rotates in a counterclockwise direction while the second flywheel rotates in a clockwise rotation. The clockwise and counterclockwise rotation of the flywheels at the same speed cancels out any vibratory forces in the x-direction thereby resulting in vibration only in the y-direction. A disadvantage of the device, however, is that it comprises a single motor and a geared driver, i.e., cog wheels, for rotating both of the flywheels. One cog wheel and its associated flywheel rotates in a clockwise direction whereas the other cog wheel and its associated flywheel rotates in a counterclockwise direction. The cog wheels are connected such that the flywheels, when rotated, rotate at the same speed. Another disadvantage is that the direction of the vibration cannot be adaptively controlled in a manner that optimizes the direction of vibration motion of the generated shear wave at the tissue location where ultrasound (US) shear wave imaging is performed. For optimal shear wave measurement, the tissue vibration motion direction should be substantially aligned with the direction of the ultrasound imaging beam.

Accordingly, an improved method and apparatus for overcoming the problems in the art is desired.

SUMMARY

In accordance with one embodiment, a vibration actuator for mechanically generating a shear wave comprises a housing, a plurality of n rotational vibrators and an accelerometer coupled to the housing, and a controller. The plurality of n rotational vibrators are disposed in a geometric arrangement configured to enable generation of a vibration vector with desired directional behavior selected from a plurality of vibration vectors of different directional behaviors, wherein n is a number of at least three. Each rotational vibrator comprises an independently controllable motor having a drive shaft and an eccentric disk coupled to the drive shaft in a plane perpendicular to an axis of the drive shaft. The accelerometer is arranged to detect a vibration vector generated by at least two of the plurality of n rotational vibrators and generate an accelerometer output signal based on the detected vibration vector. The controller is operatively coupled to each rotational vibrator for selectively controlling (i) a first set of two of the plurality of n rotational vibrators to rotate respective eccentric disks in a first coordinated manner based at least on the accelerometer output signal to produce a first vibration vector, and (ii) a second set of two of the plurality of n rotational vibrators to rotate respective eccentric disks in a second coordinated manner based at least on the accelerometer output signal to produce a second vibration vector. A directional behavior of the second vibration vector is different from a directional behavior of the first vibration vector.

In another embodiment, the controller is further for selectively controlling (iii) a third set of two of the plurality of n rotational vibrators to rotate respective eccentric disks in a third coordinated manner based at least on the accelerometer output signal to produce a third vibration vector. A directional behavior of the third vibration vector is different from the directional behavior of the second vibration vector and different from the directional behavior of the first vibration vector. In yet another embodiment, the controller is further configured for (i) determining a directional behavior of a resultant vibration vector based on (i)(a) the accelerometer output signal and (i)(b) the selectively controlled first set or second set of two of the plurality of n rotational vibrators to rotate respective eccentric disks, (ii) performing a comparison of a directional behavior of the resultant vibration vector to the desired directional behavior of the vibration vector, and (iii) adjusting the first or the second coordinated manner based on the comparison.

In yet another embodiment, the first coordinated manner or the second coordinated manner includes rotating each respective eccentric disk of the respective first set or second set of two of the plurality of n rotational vibrators at a same rotary speed, but in opposite rotational directions. In a further embodiment, the first or second coordinated manner includes controlling the respective first or second set of rotational vibrators (i) with mirror symmetry of the respective eccentric disks to produce a vector vibration along a mid-plane direction between respective eccentric disks, and (ii) without mirror symmetry of the respective eccentric disks to produce a vector vibration deviation from the mid-plane direction.

In one embodiment, the vibration actuator includes wherein each eccentric disk of a respective motor of the respective first set or second set of two of the plurality of n rotational vibrators is arranged co-planar to one another within the respective first set or second set. According to another embodiment, each respective motor comprises a bi-axial motor, and further wherein each respective eccentric disk comprises a first eccentric disk coupled to a first end of a respective drive shaft and a second eccentric disk coupled to a second end of the respective drive shaft. In yet another embodiment, each respective eccentric disk comprises a disk having an off-center weight, further wherein the respective off-center weight of respective eccentric disks of a respective first and second rotational vibrator are controlled, via the respective motor and the controller, to rotate in positions that are symmetrical to one another and to generate vibrations, wherein only vibrational components along a mid-plane between the respective first and second rotational vibrator remains, while vibrations in all other directions cancel each other.

According to another embodiment, the vibration actuator includes wherein n comprises three, and wherein the geometric arrangement of three rotational vibrators comprises a triangular arrangement. In one embodiment, the triangular arrangement comprises the three rotational vibrators having axes of their respective motor drive shafts located at apexes of a triangle, and further wherein the directional behavior of the first vibration vector and the directional behavior of the second vibration vector are selected from the group consisting of +120 degrees, 0 degrees and –120 degrees. In another embodiment, the triangular arrangement is configured to enable achievement of multiple electronically selectable vibration orientations selected from the group consisting of (i) +15 degrees, 0 degrees and –15 degrees, (ii) +20 degrees, 0 degrees and –20 degrees, (iii) +30 degrees, 0 degrees and –30 degrees, and (iv) orientations in a range from +–10 to +–110 degrees. According to yet another embodiment, the geometric arrangement further includes the number of n rotational vibrators configured to enable generation of multiple electronically selectable vibration vectors in n*(n–1)/2 directions.

In one embodiment, each rotational vibrator further comprises a position sensor arranged to detect a radial orientation or rotational angle of the respective eccentric disk and generate a respective position signal. In such an embodiment, controlling via the controller further comprises synchronously controlling, based on respective position signals, (i) the first set of two of the plurality of n rotational vibrators to rotate respective eccentric disks and produce the first vibration vector and (ii) the second set of two of the plurality of n rotational vibrators to rotate respective eccentric disks and produce the second vibration vector. In a further embodiment, the position sensor comprises at least one selected from the group consisting of an optical position sensor and an inductive sensor, and wherein the position sensor further comprises one selected from the group consisting of (i) being integrated into a respective motor of a respective rotational vibrator of the plurality of n rotational vibrators and (ii) bring an additional component coupled to the respective motor.

According to another embodiment, an ultrasound probe for shear wave elastography comprises an ultrasound transducer array for generating ultrasound waves and a vibration actuator according to embodiments disclosed herein for generating mechanically induced shear waves. The ultrasound probe further comprises an ultrasound probe controller operatively coupled to the ultrasound transducer array and the linear vibration actuator for implementing at least (i) a first mode of operation for generating and receiving ultrasound waves via the ultrasound transducer array and (ii) a second mode of operation for a combination of both (ii)(a) generating and receiving ultrasound waves and (ii)(b) generating mechanically induced shear waves via the ultrasound transducer array and the vibration actuator, respectively.

According to yet another embodiment, a system for shear wave elastography comprises an ultrasound probe according to embodiments disclosed herein, ultrasound system electronics operatively coupled to the ultrasound probe and arranged for obtaining ultrasound images in a first modality, and obtaining shear wave elastography images in a second modality. The system further comprises a display coupled to the ultrasound system electronics for displaying the obtained ultrasound and shear wave elastography images.

In one embodiment, a method for mechanically generating a shear wave via a vibration actuator, comprises providing a plurality of n rotational vibrators coupled to a housing in a geometric arrangement configured to enable generation of a vibration vector with desired directional behavior selected from a plurality of vibration vectors of different directional behaviors, wherein n is a number of at least three. Each rotational vibrator comprises an independently controllable motor having a drive shaft and an eccentric disk coupled to the drive shaft in a plane perpendicular to an axis of the drive shaft. The method further comprises detecting, via an accelerometer coupled to the housing, a vibration vector generated by at least two of the plurality of n rotational vibrators and generating an accelerometer output signal based on the detected vibration vector. In addition, the method comprises selectively controlling, via a controller operatively coupled to each rotational vibrator, (i) a first set of two of the plurality of n rotational vibrators to rotate respective eccentric disks in a first coordinated manner based at least on the accelerometer output signal to produce a first vibration vector, and (ii) a second set of two of the plurality of n rotational vibrators to rotate respective eccentric disks in a second coordinated manner based at least on the accelerometer output signal to produce a second vibration vector. A directional behavior of the second vibration vector is different from a directional behavior of the first vibration vector.

In another embodiment, the method includes the step of wherein selectively controlling, via the controller, further comprises (i) determining a directional behavior of a resultant vibration vector based on (i)(a) the accelerometer output signal and (i)(b) the selectively controlled first set or second set of two of the plurality of n rotational vibrators to rotate respective eccentric disks, (ii) performing a comparison of a directional behavior of the resultant vibration vector to the desired directional behavior of the vibration vector, and (iii) adjusting the first or the second coordinated manner based on the comparison. According to another embodiment, the first or second coordinated manner includes controlling the respective first or second set of rotational vibrators (i) with mirror symmetry of the respective eccentric disks to produce a vector vibration along a mid-plane direction between respective eccentric disks, and (ii) without mirror symmetry of the respective eccentric disks to produce a vector vibration deviation from the mid-plane direction.

In yet another embodiment, the method further comprises detecting, via a position sensor of a respective rotational vibrator, a radial orientation or rotational angle of the respective eccentric disk and generating a respective position signal based on the detected orientation or rotational angle. In such an embodiment, the method includes the step of wherein controlling, via the controller, further comprises synchronously controlling, based on respective position signals, (i) the first set of two of the plurality of n rotational vibrators to rotate respective eccentric disks and produce the first vibration vector and (ii) the second set of two of the plurality of n rotational vibrators to rotate respective eccentric disks and produce the second vibration vector.

As can be understood from this disclosure, the embodiments of the present disclosure provide various advantages over the existing solutions. Ultrasound shear wave elastography can be performed with a shear wave that is mechanically generated with a vibrator. Ultrasound tissue tracking is most effective when the shear wave motion is primarily along the direction of the ultrasound imaging beam. For computationally efficient one-dimensional (1D) tracking along an imaging beam, shear wave motion in other directions degrades tracking performance and therefore it is desirable to use the actuator according to the embodiments of the present disclosure to align shear wave motion along the direction of a steered ultrasound imaging beam. In addition, rotational vibrators are very efficient at generating large vibration strength in a small form factor. However, rotational vibrators vibrate in a circular manner which, if uncoordinated, results in tissue displacement in multiple directions different from the direction of ultrasound tracking beams. The vibration actuator, system and method according to the embodiments of the present disclosure advantageously enable generation of linear vibration using multiple coupled rotational vibrators operating in a coordinated manner, producing linear vibration in a compact and energy efficient form factor.

Still further advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1:
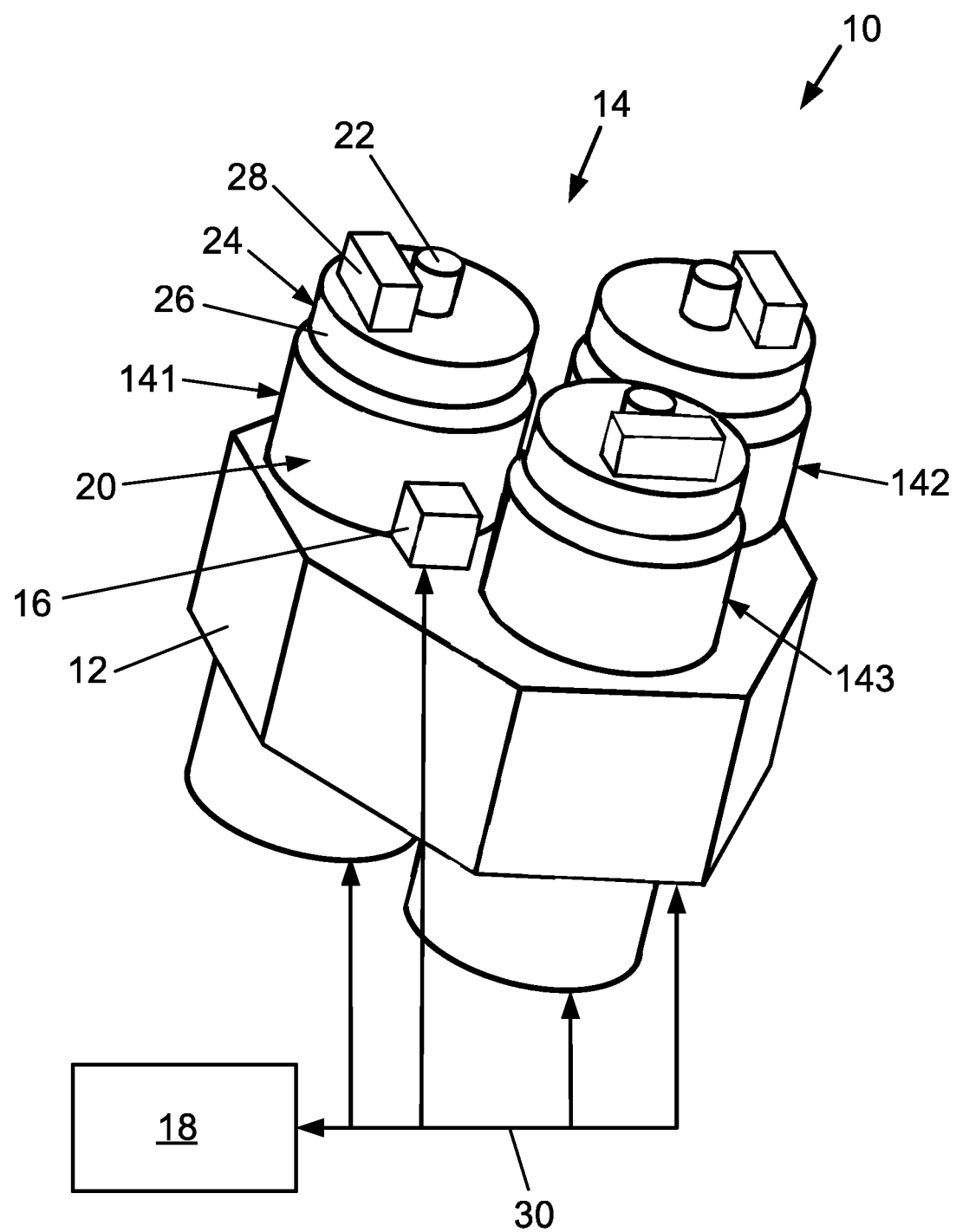
FIG. 1 is a block diagram and perspective view of the vibration actuator according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

With reference now to FIG. 1, there is shown a block diagram/perspective view of the vibration actuator 10 for mechanically generating a shear wave according to an embodiment of the present disclosure. The vibration actuator 10 comprises a housing 12, a plurality of n rotational vibrators, generally indicated by the reference numeral 14, an accelerometer 16, and a controller 18. In a preferred embodiment, the designation n comprises a number of at least three. In one embodiment, the plurality of n rotational vibrators 14, as shown in FIG. 1, comprises three rotational vibrators. The three rotational vibrators are indicated by reference numerals 141, 142 and 143, representative of a first rotational vibrator, a second rotational vibrator and a third rotational vibrator, respectively. Each of the rotational vibrators are substantially identical to one another and thus details of only one rotational vibrator shall be discussed herein for simplicity of explanation.

The first rotational vibrator 141 comprises an independently controllable DC motor 20 coupled to the housing 12 and having a rotary drive shaft 22 extending from a main body of the motor. An eccentric disk 24 is fixed coupled to the drive shaft 22 for rotation about a longitudinal axis of the drive shaft, the eccentric disk residing in a plane perpendicular to the longitudinal axis of the drive shaft 22. In one embodiment, the eccentric disk 24 comprises a disk 26 having an off-center weight 28. In another embodiment, the eccentric disk is a mass of any shape with the functional ability to act as an off-center weight or eccentrically rotating object. As noted herein above, the rotational vibrators are substantially identical to one another. Accordingly, the discussion of the independently controllable DC motor, rotary drive shaft, and eccentric disk with respect to the first rotational vibrator 141 apply equally to that of the second and third rotational vibrators 142 and 143, respectively. In addition, as will be discussed further herein below, the plurality of n rotational vibrators 14 are coupled to the housing 12 in a geometric arrangement configured to enable generation of a vibration vector with desired directional behavior selected from a plurality of distinct electronically selectable vibration vectors of different directional behaviors.

With reference still to FIG. 1, the accelerometer 16 is coupled to the housing 12. The accelerometer 16 comprises any suitable accelerometer arranged to (i) detect a vibration vector, e.g., a resultant vibration vector, generated by at least two of the plurality of n rotational vibrators 14 and (ii) generate an accelerometer output signal based on the detected vibration vector, as will be discussed further herein below.

In one embodiment, controller 18 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given vibration actuator implementation and/or application. Controller 18 can further comprise one or more of various modules, units, or subsystems, including for example, a motor controller.

Figure 2:
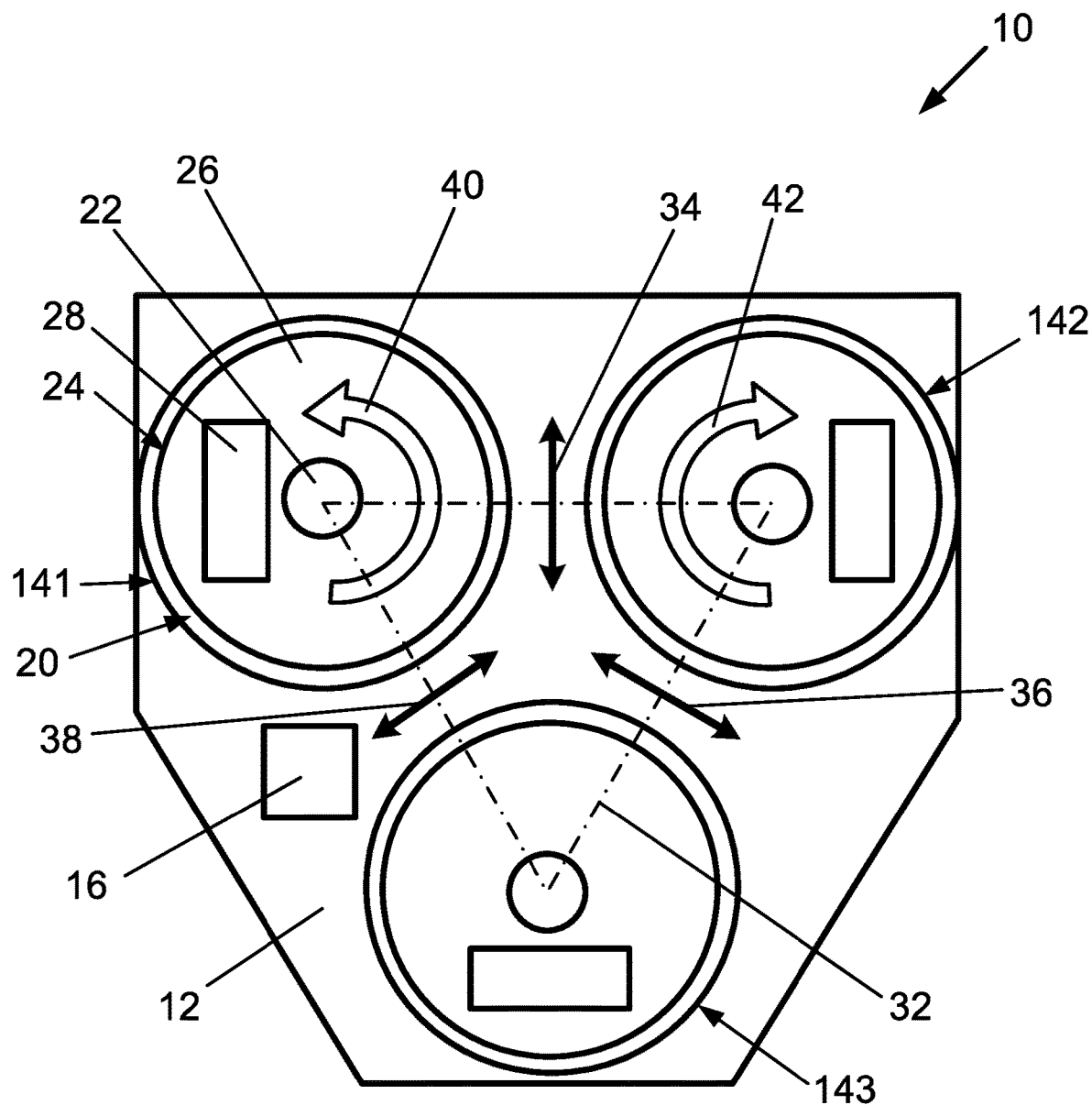
FIG. 2 is a top view of the vibration actuator of FIG. 1 according to one embodiment of the present disclosure.

With reference now to FIGS. 1 and 2, in one embodiment, the designation n comprises three, and the geometric arrangement, as indicated by reference numeral 32, of three rotational vibrators 141, 142 and 143 comprises a triangular arrangement. With respect to the triangular arrangement, the three rotational vibrators 141, 142 and 143 have axes of their respective DC motor drive shafts 22 located at apexes of a triangle. In the case of an equilateral triangle, the directional behavior of the first shear wave vibration vector and the directional behavior of the second shear wave vibration vector are selected from the group consisting of +120 degrees, 0 degrees and −120 degrees, as will become apparent from the disclosure herein below. In other embodiments, the triangular arrangement is configured with respective motor drive shafts located at apexes of a given triangle to enable achievement of multiple electronically selectable vibration orientations selected from the group consisting of (i) +15 degrees, 0 degrees and −15 degrees, (ii) +20 degrees, 0 degrees and −20 degrees, (iii) +30 degrees, 0 degrees and −30 degrees, and (iv) orientations in a range from +−10 to +−110 degrees.

Referring still to FIGS. 1 and 2, the controller 18 operatively couples to each DC motor of a respective rotational vibrator of the plurality of n rotational vibrators 14 and to the accelerometer 16, via power/signal lines, generally indicated by reference numeral 30 (FIG. 1). The controller 18 is adapted to selectively control (i) a first set of two (e.g., 141 and 142, FIG. 2) of the plurality of n rotational vibrators to rotate respective eccentric disks 24 in a first coordinated manner based at least on the accelerometer output signal to produce a first shear wave vibration vector, indicated by reference numeral 34 in FIG. 2. Controller 18 is further adapted to selectively control (ii) a second set of two (e.g., 142 and 143, FIG. 2) of the plurality of n rotational vibrators to rotate respective eccentric disks in a second coordinated manner based at least on the accelerometer output signal to produce a second shear wave vibration vector, indicated by reference numeral 36 in FIG. 2. It is noted that a directional behavior of the second shear wave vibration vector 36 is different from a directional behavior of the first shear wave vibration vector 34.

In addition, the controller 18 is further adapted to selectively control (iii) a third set of two (e.g., 143 and 141, FIG. 2) of the plurality of n rotational vibrators 14 to rotate respective eccentric disks in a third coordinated manner based at least on the accelerometer output signal to produce a third shear wave vibration vector, indicated by reference numeral 38 in FIG. 2. It is further noted that a directional behavior of the third shear wave vibration vector 38 is different from the directional behavior of the second shear wave vibration vector 36 and different from the directional behavior of the first shear wave vibration vector 34. Accordingly, with the embodiment of FIGS. 1 and 2, the geometric arrangement 32 of the plurality of three rotational vibrators 141, 142, and 143 coupled to the housing 12 in the form of a triangle enables generating a vibration vector with desired directional behavior selected from a plurality of distinct electronically selectable vibration vectors of different directional behaviors, e.g., as indicated by reference numerals 34, 36 and 38.

With reference still to FIGS. 1 and 2, in one embodiment, the first coordinated manner or the second coordinated manner includes rotating each respective eccentric disk of the respective first set or second set of two of the plurality of n rotational vibrators 14 at a same rotary speed, but in opposite rotational directions. With reference to FIG. 2, a first arrow, indicated by reference numeral 40, is indicative of the respective drive shaft 22 and eccentric disk 24 of the first rotational vibrator 141 being rotated in a counter clockwise rotation direction. A second arrow, indicated by reference numeral 42, is indicative of the respective drive shaft and eccentric disk of the second rotational vibrator 142 being rotated in a clockwise rotation direction. In addition, in one embodiment, each eccentric disk 24 of a respective DC motor 20 of the respective first set (e.g., 141 and 142), or second set (e.g., 142 and 143) of two of the plurality of n rotational vibrators 14 is arranged co-planar to one another within the respective first set or second set.

In another embodiment, the first or second coordinated manner further includes controlling the respective first or second set of rotational vibrators (i) with mirror symmetry of the respective eccentric disks to produce a vector vibration along a mid-plane direction between respective eccentric disks, and (ii) without mirror symmetry of the respective eccentric disks to produce a vector vibration deviation from the mid-plane direction (not shown, but would include a deviation from the mid-plane direction 34, i.e., a direction other than the mid-plane direction 34). The illustration in FIG. 2 of the first and second rotational vibrators 141 and 142, respectively, is just one example of mirror symmetry of the respective eccentric disks of first and second rotational vibrators 141 and 142, respectively, which produces the vector vibration along the mid-plane direction between the respective eccentric disks, as indicated via reference numeral 34. For instance, eccentric disk 24 of the first rotational vibrator 141 can be controlled to rotate in the counter clockwise direction 40 and at the same time that the eccentric disk of the second rotational vibrator 142 can be controlled to rotate in the clockwise direction 42. For mirror symmetry, the weight 28 of the eccentric disk 24 of the first rotational vibrator 141 rotates about the respective drive shaft 22 in which the weight's location, as it rotates about the respective drive shaft, is a mutual mirror image to the location of the weight of the eccentric disk of the second rotational vibrator 142 as the later weight rotates about its respective drive shaft. The mutual mirror image is about a mirror plane which is disposed perpendicular to the plane of respective eccentric disks, and half-way therebetween, of the first and second rotational vibrators. In addition, to assist in a better understanding of non-mirror symmetry, with reference still to FIG. 2, consider the example of the non-mirror symmetry of respective eccentric disks of first and third rotational vibrators 141 and 143. Assuming that the eccentric disk of the third rotational vibrator is rotating in a clockwise direction, the eccentric disks of the first and third rotational vibrators would not possess mirror symmetry at any given moment in time of rotation with respect to one another and thus would produce a vector vibration that deviates from, or has a direction other than, the mid-plane direction 38.

In other words, in an embodiment with mirror symmetry, the respective off-center weight of respective eccentric disks of a respective first and second rotational vibrator are controlled, via the respective DC motor and the controller 18, to rotate in positions that are symmetrical to one another and to generate vibrations, wherein only vibrational components along a mid-plane between the respective first and second rotational vibrator remains, while vibrations in all other directions cancel each other. On the other hand, controlling the first and second rotational vibrators 141 and 142, respectively, without mirror symmetry of the respective eccentric disks would produce a vector vibration deviation from the mid-plane direction (not shown), i.e., a deviation from the mid-plane direction indicated by reference numeral 34. The third coordinated manner is similar to that of the first or second coordinated manner and can include controlling respective rotational vibrators with mirror symmetry or without mirror symmetry, as discussed herein above.

In the embodiment of FIG. 2, the geometric arrangement 32 of the three rotational vibrators comprises a triangular arrangement in the form of an equilateral triangle. With mirror symmetry, the directional behavior of the first shear wave vibration vector 34 is 0 degrees. The directional behavior of the second shear wave vibration vector 36 is −120 degrees. Lastly, the directional behavior of the third shear wave vibration vector 38 is +120 degrees. With respect to a geometric arrangement 32 comprising a triangular arrangement, wherein the triangular arrangement is in the form of a given triangle other than an equilateral triangle, the triangular arrangement can be configured to enable achievement of multiple electronically selectable vibration orientations. In one example, the position of the three rotational vibrators can be configured in a triangular arrangement so that the three electronically selectable vibration orientations are closer to each other, e.g., differing by 20 degrees instead of 120 degrees, meaning the vibration force can vary with increments of 20 degrees: +20, 0 and −20 degree. The multiple electronically selectable vibration orientations can also be selected from the group consisting of (i) +15 degrees, 0 degrees and −15 degrees, (ii) +20 degrees, 0 degrees and −20 degrees, (iii) +30 degrees, 0 degrees and −30 degrees, and (iv) orientations in a range from +−10 to +−110 degrees. Still further electronically selectable vibration orientations are contemplated, e.g., +20 degrees, 0 degrees and −25 degrees, and the like, according to the requirements of a particular vibration actuator implementation.

In another embodiment, the geometric arrangement further includes the number of n rotational vibrators configured to enable generation of multiple electronically selectable vibration vectors in $n*(n-1)/2$ directions. Accordingly, a vibration actuator having four rotational vibrators enables generation of multiple electronically selectable vibration vectors in six directions (i.e., $4*(4-1)/2=6$ directions). An example of such a vibration actuator will be discussed further herein below with respect to the embodiment of FIG. 5. The number of n rotational vibrators is not limited to three or four, but can be any number of rotational vibrators configured in a geometric arrangement to enable generation of multiple electronically selectable vibration vectors for a given vibration actuator implementation and/or application. In one embodiment, the vibration actuator comprises a linear vibration actuator with at least three rotational vibrators for mechanically generating electronically selectable vibration vectors or shear waves in at least two different directions. In another embodiment, the vibration actuator can comprise at least three rotational vibrators for generating electrically selectable vibrations vectors in modes of vibration that are not purely linear.

Referring again to FIGS. 1 and 2, the controller 18 is further configured for (i) determining a directional behavior of a resultant vibration vector based on (i)(a) the accelerometer output signal and (i)(b) the selectively controlled first set (e.g., 141 and 142) or second set (e.g., 142 and 143) of two of the plurality of n rotational vibrators 14 to rotate respective eccentric disks, (ii) performing a comparison of a directional behavior of the resultant vibration vector to the desired directional behavior of the vibration vector, and (iii) adjusting the first or the second coordinated manner based on the comparison. In this manner, the controller performs feedback control of the directional behavior of the resultant vibration vector to maintain a desired directional behavior of the resultant vibration vector. In other words, synchronization can be achieved by driving the rotational vibrators with speed regulating electronics of the controller 18 in a control loop employing sensors (e.g., accelerometer and position sensors) for monitoring aspects of the vibration activity.

In one example of the present disclosure, three rotational vibrators are rigidly attached to each other, e.g., via housing 12, in such a way that the off-balance weights 28 of respective eccentric disks 24 are configured to spin in a same plane. Each of the rotational vibrators are physically coupled with respect to each other, but can spin independently. The accelerometer 16 serves as a sensor in an electronic control loop, wherein the controller 18 or control electronics coordinates independent motion of each respective eccentric disk between the individual vibrators to achieve a desired vibration behavior and/or pattern.

With respect to achieving linear vibration, only two out of the three rotational vibrators of FIGS. 1 and 2 are activated in opposite spin directions, while the third rotational vibrator does not spin. As shown by the arrows 40 and 42 in FIG. 2, to get an up/down linear vibration, shear wave force, indicated by reference numeral 34, the first rotational vibrator 141 and the second rotational vibrator 142 are used. In a similar manner, using a second pair of rotational vibrators 141 and 143, or a third pair of rotational vibrators 142 and 143, can change the orientation of the linear vibration or shear wave force by +120 and −120 degrees, respectively. Thus, the vibration actuator 10 can electronically switch between three different orientations for the linear vibration force. This electronic switching of vibration force orientation can help optimize an angle between a mechanical shear wave and ultrasound tracking beam for different tissue regions of interest, for example. Note that the wave front of shear waves generated by mechanical vibration depends on the vibration direction of the vibration actuator 10.

In one embodiment, a correct coordinated motion for linear vibration is achieved by looking at the accelerometer signal. When two rotational vibrators of the vibration actuator are spinning exactly symmetrically, there is only linear vibration force along one axis in the plane containing the three eccentric disks, a situation that is maintained by a control loop, via the controller. As soon as a position of one rotational vibrator starts to drift away from the other one and the two rotational vibrators go out of mirror symmetry, an additional perpendicular vibration component is the plane with the three eccentric disks starts to appear. The control loop operates to adjust speed of one rotational vibrator relative to the other to minimize, constantly or at a given adjustment duty cycle, the perpendicular vibration component.

Figure 3:
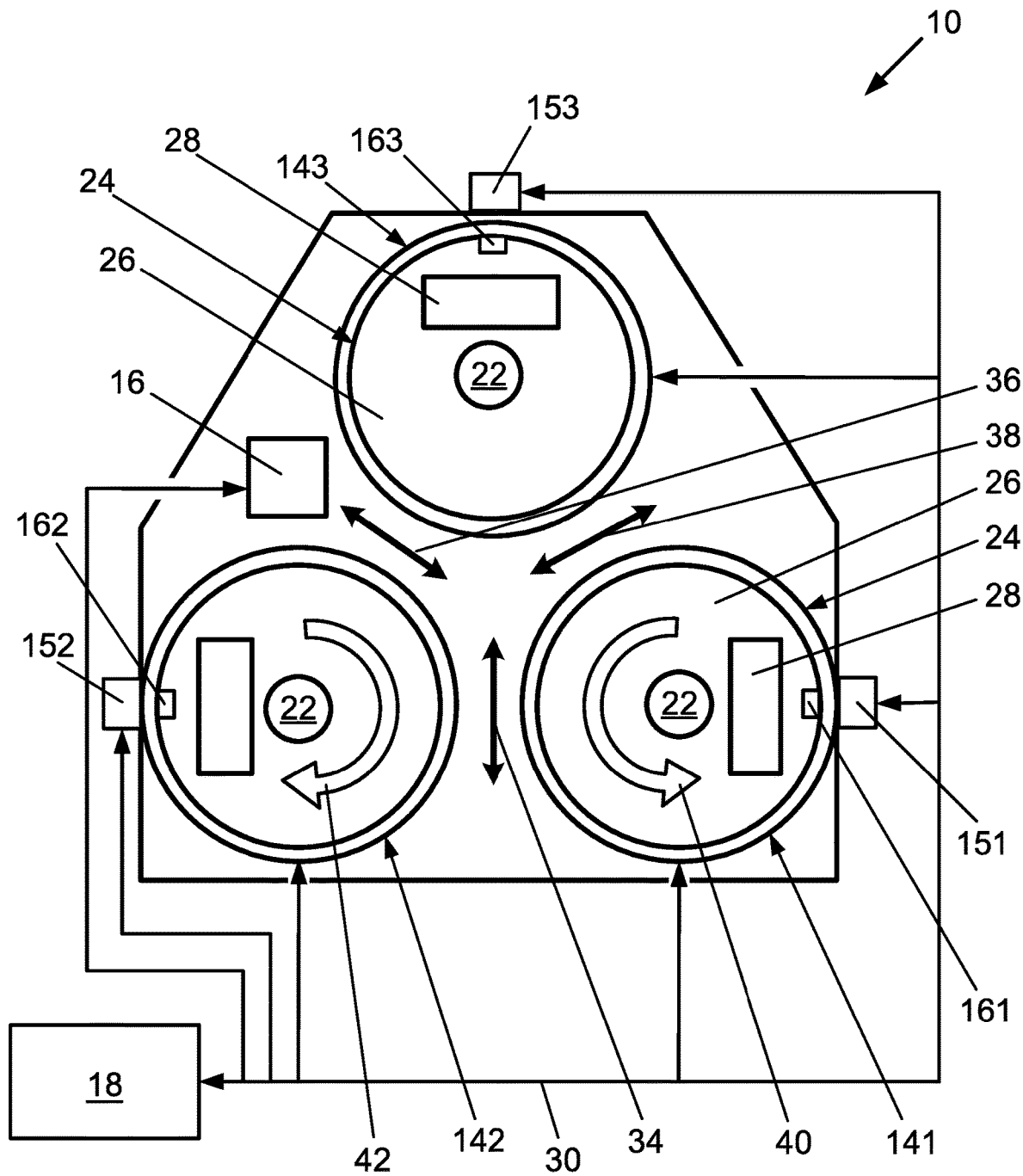
FIG. 3 is a block diagram top view of the vibration actuator of FIG. 1 according to another embodiment of the present disclosure.

With reference now to FIG. 3, there is shown a block diagram top view of the vibration actuator of FIG. 1 according to another embodiment of the present disclosure. The embodiment of FIG. 3 is similar to that of the embodiment of FIG. 1, the discussion of which equally applies to the embodiment of FIG. 3, with the following differences. Each rotational vibrator 141, 142 and 143 further comprises a position sensor 151, 152, and 153, respectively, arranged to detect a radial orientation or rotational angle of the respective eccentric disk 24 of the rotational vibrator 141, 142 and 143. In addition, each position sensor 151, 152, and 153 is further arranged to generate a respective position signal indicative of the radial orientation or rotational angle of the respective eccentric disk 24 of the rotational vibrator 141, 142 and 143. The controller 18 is further operatively coupled to the position sensors 151, 152 and 153 via power/signal lines, generally indicated by reference numeral 30. In operation, controlling via the controller 18 further comprises synchronously controlling, based on respective position signals, (i) the first set (e.g., 141 and 142) of two of the plurality of n rotational vibrators 14 to rotate respective eccentric disks 24 and produce the first vibration vector (e.g., 34) and (ii) the second set (e.g., 142 and 143) of two of the plurality of n rotational vibrators 14 to rotate respective eccentric disks 24 and produce the second vibration vector (e.g., 36).

In one embodiment, each position sensor 151, 152 and 153 comprises at least one selected from the group consisting of an optical position sensor and an inductive sensor. For the embodiment with the optical position sensors, the position sensor 151, 152 and 153 comprises an additional component coupled to the DC motor 20 of a respective rotational vibrator 141, 142 and 143 of the plurality of n rotational vibrators 14. In addition, the optical position sensors cooperate with a respective position indicator/reference 161, 162 and 163 of the eccentric disks 24 of a respective rotational vibrator 141, 142 and 143 of the plurality of n rotational vibrators 14. The respective position indicator/reference 161, 162 and 163 enables the corresponding optical position sensor to generate a respective position signal indicative of the radial orientation or rotational angle of the eccentric disk 24 of the respective rotational vibrator 141, 142 and 143. The radial orientation or rotational angle information, via the respective position signals, enables synchronization and/or mirror symmetry, via the controller 18, of a given pair of eccentric disks with respect to one another.

Figure 4:
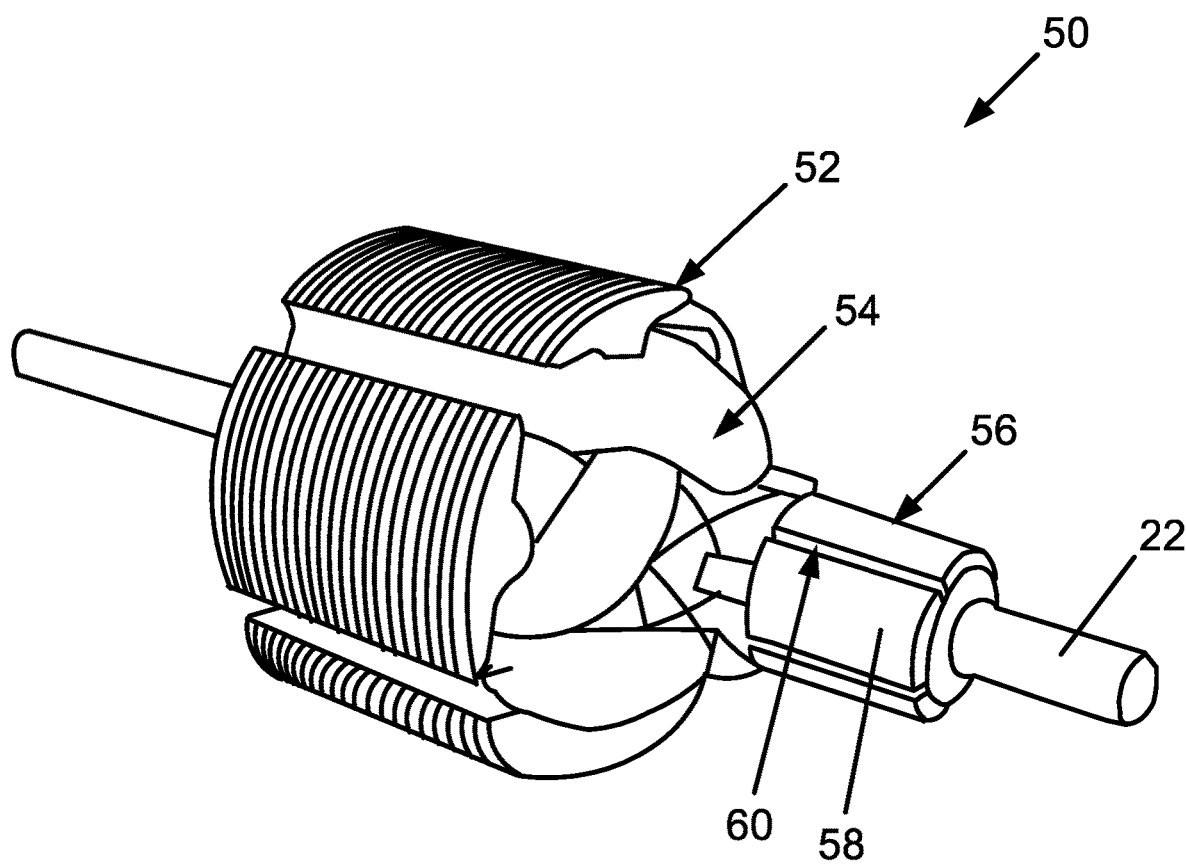
FIG. 4 is an illustrative perspective diagram view of an internal component of a rotational motor of the vibration actuator of FIG. 1 according to an embodiment of the present disclosure.

For the embodiment with an inductive sensor, the position sensor is integrated into the DC motor 20 of a respective rotational vibrator 141, 142 and 143 of the plurality of n rotational vibrators 14 and will be discussed further herein with reference to FIGS. 3 and 4. FIG. 4 illustrates a perspective diagram view of an internal component of the DC motor 20 of a rotational vibrator (141, 142 or 143) of the vibration actuator 10 of FIG. 1. The component comprises, for example, a rotor 50 that includes the drive shaft 22, a plurality of metal laminations 52 coupled to the drive shaft, a plurality of rotor windings 54 wrapped in a designated manner about the inner portions of the metal laminations 52 as is known in the art, and a commutator 56 made up of multiple commutator plates or segments 58. Each commutator plate or segment is separated from an adjacent commutator segment via a gap, such as indicate by reference numeral 60.

In one embodiment, all gaps 60 are of a given equal dimension except at least one of different dimensions. The at least one gap of different dimensions provides for a given inductive electrical characteristic which can be detected, via an inductive sensor, during operation of the motor. The given electrical characteristic can provide a respective position signal, as a function of the at least one gap of different dimensions. The position signal is indicative of the radial orientation or rotational angle of the eccentric disk 24 of the respective rotational vibrator 141, 142 and 143 in view of the eccentric disk 24 being fixedly coupled to the motor shaft of the DC motor. The radial orientation or rotational angle information, via respective position signals, enables synchronization and/or mirror symmetry, via the controller 18, of a given pair of eccentric disks with respect to one another.

In other words, in contrast to a standard 4-plate commutator, one could create a slight asymmetry in the commutator plates 58, for example, by increasing one of the gaps between plates. This would result in a current disturbance pattern detectable by suitable driving electronics of controller 18. Alternatively, one could increase or decrease the number of windings in one of the rotor windings 54, or put a detectable electronic component in parallel with one of the rotor windings 54.

In one embodiment, motion coordination can also be done, via the controller 18, through an electronic control loop in which the feedback is also based upon signals from the position sensors. As shown in FIG. 3, each rotational vibrator has a corresponding position sensor. Each position sensor could, for example, providing an indication, via a position sensor signal, each time the weight 28 of a respective eccentric disk 24 is at a zero degree (0°) rotational angle.

Figure 5:
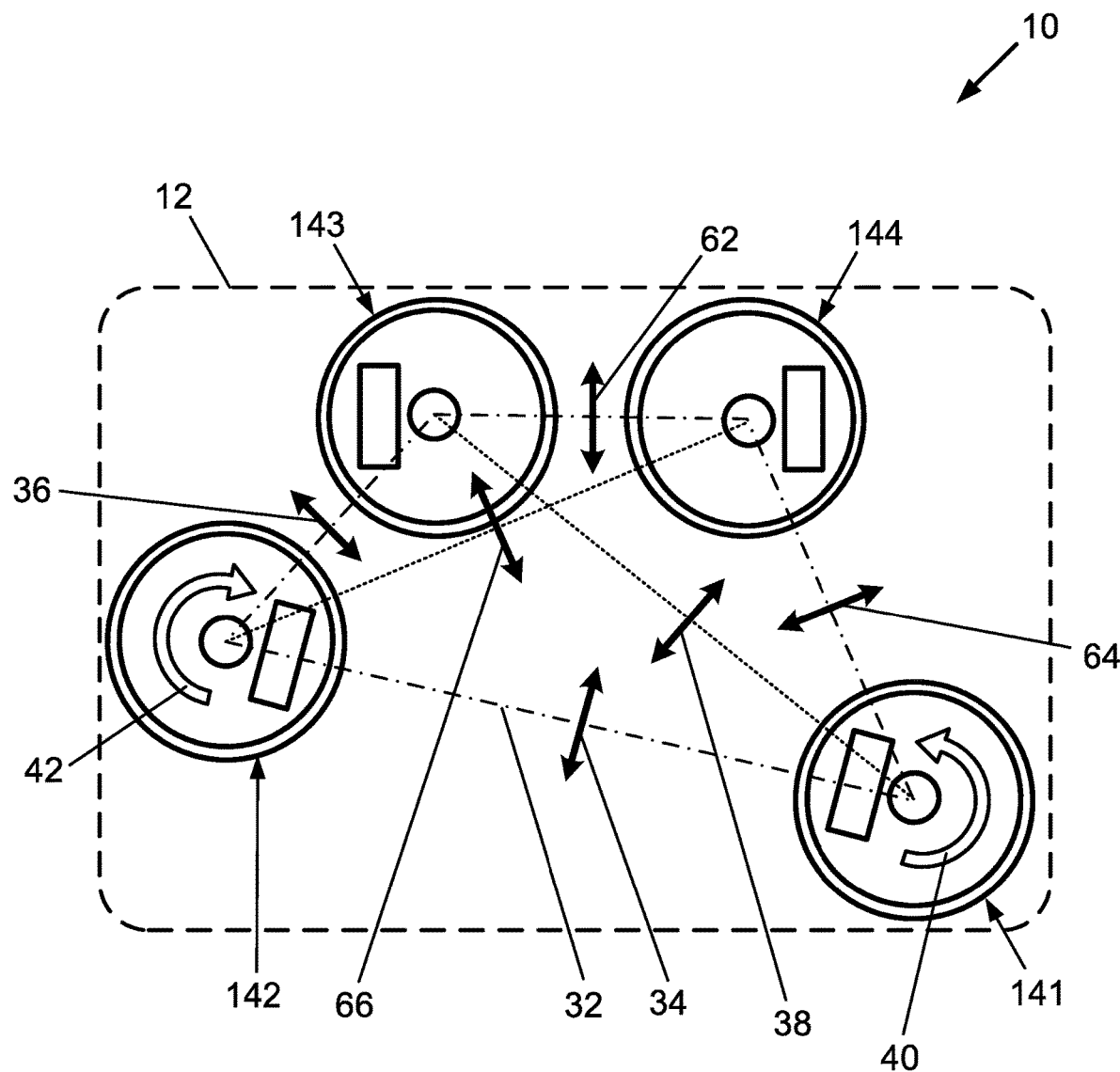
FIG. 5 is a top view of a vibration actuator according to another embodiment of the present disclosure.

With reference now to FIG. 5, there is shown a top view of a vibration actuator 10 according to another embodiment of the present disclosure. The embodiment of FIG. 5 is similar to that of the embodiment of FIG. 1, the discussion of which equally applies to the embodiment of FIG. 5, with the following differences. The geometric arrangement 32 includes a plurality of four rotational vibrators 141, 142, 143 and 144 coupled to the housing 12 in the form of a quadrilateral. That is, the four rotational vibrators 141, 142, 143 and 144 have axes of their respective DC motor drive shafts 22 located at apexes of the quadrilateral. The geometric arrangement 32 in the form of the quadrilateral enables generating a vibration vector with desired directional behavior selected from a plurality of distinct electronically selectable vibration vectors of different directional behaviors, e.g., as indicated by reference numerals 34, 36, 38, 62, 64 and 66. As discussed herein above, the geometric arrangement 32 includes the number of n rotational vibrators configured to enable generation of multiple electronically selectable vibration vectors in n*(n−1)/2 directions. Accordingly, the embodiment of the vibration actuator 10 having four rotational vibrators 141, 142, 143 and 144 as shown in FIG. 5 enables generation of multiple electronically selectable vibration vectors in six directions (i.e., 4*(4−1)/2=6 directions).

Figure 6:
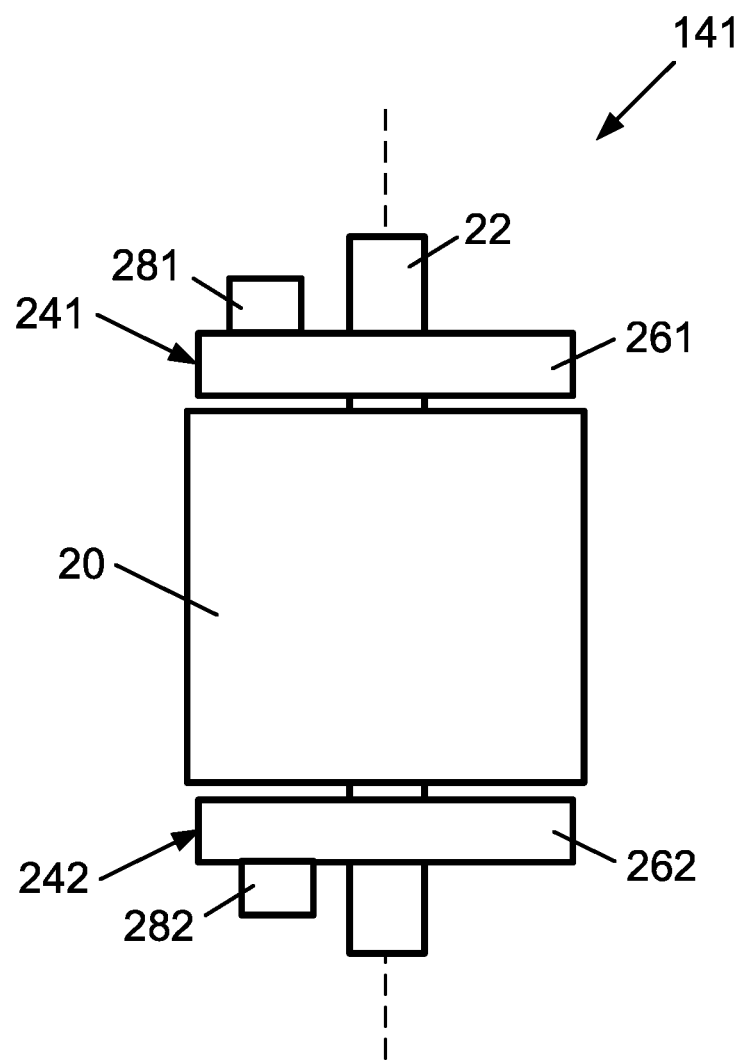
FIG. 6 is a side view of a rotational vibrator of the vibration actuator according to another embodiment of the present disclosure.

With reference now to FIG. 6, there is shown a side view of a rotational vibrator, for example, rotational vibrator 141, according to another embodiment of the present disclosure. The embodiment of FIG. 6 is similar to that of the embodiment of FIG. 1, the discussion of which equally applies to the embodiment of FIG. 6, with the following differences. In this embodiment, each respective DC motor 20 comprises a bi-axial motor, and further wherein each respective eccentric disk 24 comprises a first eccentric disk 241 fixedly coupled to a first end of a respective drive shaft 22 and a second eccentric disk 262 fixedly coupled to a second end of the respective drive shaft 22, opposite the first end. The first eccentric disk 241 and the second eccentric disk 242 are coupled to the drive shaft 22 in a mirror symmetric manner, as shown in FIG. 6. With the configuration of the bi-axial motor and first and second eccentric disks 241 and 242, respectively, the weight of the single eccentric disk 24 per rotational vibrator in FIG. 1 can be divided in half and equally distributed between the first and second eccentric disks 241 and 242, respectively. As a result, undesirable strain on the DC motor drive shaft can be advantageously reduced, compared to that of having the eccentric disk only at one end of the DC motor drive shaft.

Figure 7:
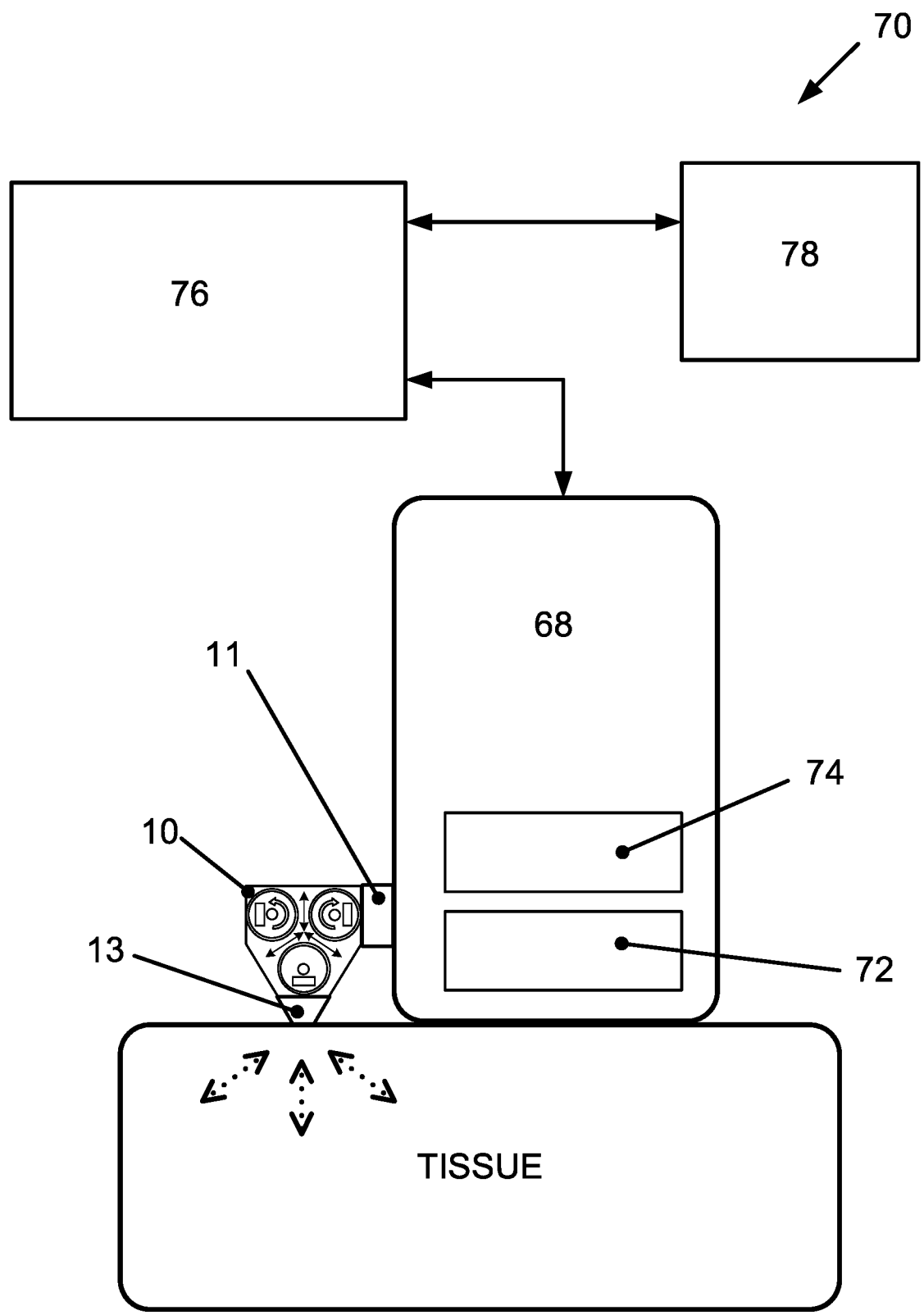
FIG. 7 is a block diagram view of an ultrasound probe and ultrasound system incorporating the vibration actuator according to another embodiment of the present disclosure.

Turning now to FIG. 7, a block diagram view of an ultrasound probe 68 and ultrasound system 70 incorporating the vibration actuator 10 according to another embodiment of the present disclosure is shown. The ultrasound probe 68 is configured for shear wave elastography and comprises an ultrasound transducer array 72 and an ultrasound probe controller 74. The ultrasound probe 68 further comprises a vibration actuator 10 according to one or more of the various embodiments of the present disclosure, as disclosed herein. The ultrasound probe 68 further comprises a housing suitable for a given ultrasound probe implementation, wherein the ultrasound transducer array 72, the ultrasound probe controller 74 and the vibration actuator 10 are arranged with respect to the ultrasound probe housing according to a particular implementation. For example, an orientation and/or placement of the vibration actuator 10 with respect to the ultrasound transducer array 72 with respect to the ultrasound probe housing is determined at least in part as a function of (i) generating and receiving ultrasound waves and (ii) generating mechanically induced shear waves, as appropriate, to enable a cost-effective elastography implementation for determining tissue elasticity with a given ultrasound platform and/or probe.

In one embodiment, the vibration actuator 10 is coupled to the housing of the ultrasound probe 68 via a vibration isolation attachment member 11. The attachment member 11 is configured to provide desired vibration isolation characteristics between the vibration actuator 10 and the housing of the ultrasound probe 68 for a given ultrasound probe implementation. The attachment member 11 can comprise any suitable form of vibration damping mechanism to prevent the ultrasound imaging probe aperture itself from vibrating and undesirably introducing shear waves into the tissue. In addition, the vibration actuator 10 further comprises a vibration coupler 13 coupled to housing of the vibration actuator 10. The vibration coupler 13 is configured to provide a desired vibration device orientation and coupling between the vibration actuator 10 and a tissue of a subject, or similar matter of an object, for which shear wave elastography is to be applied. For example, it is desirable to introduce vibration into the tissue through a relatively small contact area (i.e., via the vibration coupler 13 at the tissue surface), so that from the tissue perspective, vibration is caused by something more like to a point source. In other words, the whole transducer housing will not be vibrating. Accordingly, the vibration coupler 13 comprises a small protrusion that would be contacting the surface of tissue.

As shown in FIG. 7, the dashed arrows within the tissue show the vibration directions of shear waves that can be generated within the tissue, to accommodate ultrasound imaging beams that go straight down, or are steered left or right. It is also noted that the vibration direction of the actuator 10 may be adjusted or altered, via controller 18 and/or controller 74. An adjustment in the vibration direction could be in response to refraction effects from the tissue that cause a change in the direction of the resulting vibration motion. The vibration direction can thus be advantageously aligned with respect to the tracking beam direction at the region of interest. While FIG. 7 illustrates one example of vibrator orientation relative to skin or tissue and the probe housing, other embodiments for integrating a vibration module with an ultrasound probe are possible.

In addition, the vibration actuator 10 features a vibration vector reference (not shown) which is designated as a reference from which a remainder of vibration vectors produced by the rotational vibrators are determined for a given vibration actuator. In other words, the vibration vector reference can comprise a specific reference point or line on a side or portion of the housing 12 located between two given rotational vibrators, further corresponding to the side or portion of the housing which would face the skin of a subject when the vibration actuator 10 is in use. Push pulses generated via the vibration actuator 10 for a given tissue elasticity determination preferably emanate from the side of the vibration actuator 10 facing the skin of the subject for a given elastography implementation. It is contemplated that more than one side of the vibration actuator housing may be useful in some implementations. Furthermore, with reference again to FIG. 2, the vibration vector reference could comprise a reference point and/or line (i.e., the line extending perpendicular to the page of the drawing) on the top wall of housing 12 in FIG. 2, located mid-way between the first and second rotational vibrators 141 and 142, respectively. Other locations of specific vibration vector reference are possible, i.e., depending on the specific vibration actuator and ultrasound probe implementation. Furthermore, the spatial relationship between respective rotational vibrators is known via a given construction of a particular vibration actuator.

The ultrasound probe controller 74 is operatively coupled to the ultrasound transducer array 72 for causing the ultrasound transducer array 72 to generate and receive ultrasound waves, as is known in the art. The ultrasound probe controller 74 is further operatively coupled to the vibration actuator 10 for causing the vibration actuator 10 to generate mechanically induced shear waves, including shear waves with a desired directional behavior, as discussed herein. The generation of mechanically induced shear waves is further in coordination with generating and receiving ultrasound waves, via ultrasound transducer array 72, using suitable elastography techniques known in the art.

In one embodiment, the ultrasound probe controller 74 is operatively coupled to the ultrasound transducer array 72 and the vibration actuator 10 for implementing at least (i) a first mode of operation for generating and receiving ultrasound waves via the ultrasound transducer array 72 and (ii) a second mode of operation for a combination of both (ii)(a) generating and receiving ultrasound waves and (ii)(b) generating mechanically induced shear waves via the ultrasound transducer array 72 and the vibration actuator 10, respectively. Ultrasound probe 68 is highly suitable for a low-cost ultrasound system configured for elastography in diagnosis of liver disease by hepatologists, emergency medical diagnosis, or a military medical diagnosis in the field, for example. In addition, ultrasound probe 68 with vibration actuator 10 advantageously enables generation of linear vibration using multiple coupled rotational vibrators operating in a coordinated manner, for producing linear vibration in a compact and energy efficient form factor. The latter is in contrast to high-cost prior art systems that generate shear waves via a special acoustic push pulse with special requirements on imaging probe design and driving electronics.

With reference still to FIG. 7, according to another embodiment, an ultrasound system 70 for shear wave elastography is shown. The ultrasound system 70 includes ultrasound probe 68 as discussed herein above. Ultrasound system 70 further includes ultrasound system electronics 76 and a display 78. The ultrasound probe and display are operatively coupled to the ultrasound system electronics. In particular, the ultrasound system electronics 74 is operatively coupled to the ultrasound probe 68 and arranged for obtaining ultrasound images in a first modality, and obtaining shear wave elastography images in a second modality. Ultrasound system electronics 76 can include any suitable ultrasound system controller and associated electronics for performing shear wave elastography. Shear wave elastography and determining tissue elasticity via shear waves can be accomplished using suitable elastography techniques known in the art.

For example, the ultrasound system electronics 76 can comprise one or more of microprocessor, microcontroller, field programmable gate array (FPGA), integrated circuit, discrete analog or digital circuit components, hardware, software, firmware, or any combination thereof, for performing various functions as discussed herein and further for a given shear wave elastography ultrasound system implementation and/or application. Ultrasound system electronics 76 can further comprise one or more of various modules, units, or subsystems, power source, memory, input/output device, user interface, tactile output device, touch screen, optical display, microphone, keypad, keyboard, pointing device, image capture device, video camera, audio output device, and any combination thereof, selected as appropriate according to the requirements of the given shear wave elastography ultrasound system implementation and/or application. In one embodiment, display 78 is operatively coupled to the ultrasound system electronics 76 for displaying the obtained ultrasound and shear wave elastography images, according to the requirements of a given shear wave elastography ultrasound system implementation.

Further with reference to FIG. 7, in other embodiments, systems and methods incorporating the vibration actuator 10 and/or vibration actuation of the present disclosure are performed on an ultrasound imaging apparatus 70 configured to control one or more transducer arrays 72 to transmit ultrasound waves and receive echoes for generating ultrasound images based on the echoes. The ultrasound imaging apparatus may include processors, beamformers, and electronic circuitry (e.g., collectively indicated via ultrasound system electronics 76) as needed for signal processing and image generation. The ultrasound transducer arrays may be configured to generate 1D, 2D, and/or 3D images. The transducer arrays may be incorporated into a probe, patch, or other configuration. The ultrasound imaging system may be operable for imaging in a variety of different modalities (e.g., B-mode, M-mode, PW Doppler, spectral Doppler, etc.). For example, the imaging apparatus may be an ultrasound imaging system implemented on a hand-held device (e.g., tablet, smartphone, etc.) such as the VISIQ™ or LUMIFY™ ultrasound systems provided by PHILIPS). In some examples, the imaging apparatus may be an ultrasound imaging system implemented in a more conventional form factor, e.g., as larger but still typically portable base, which may provide a variety of imaging functions (e.g., B-mode, M-mode, color flow Doppler, PW Doppler, spectral Doppler, and other ultrasound imaging modes). For example, the imaging apparatus may be an ultrasound imaging system such as the SPARQ™ or EPIQ™ ultrasound systems provided by PHILIPS. Other ultrasound systems may be used.

Figure 8:
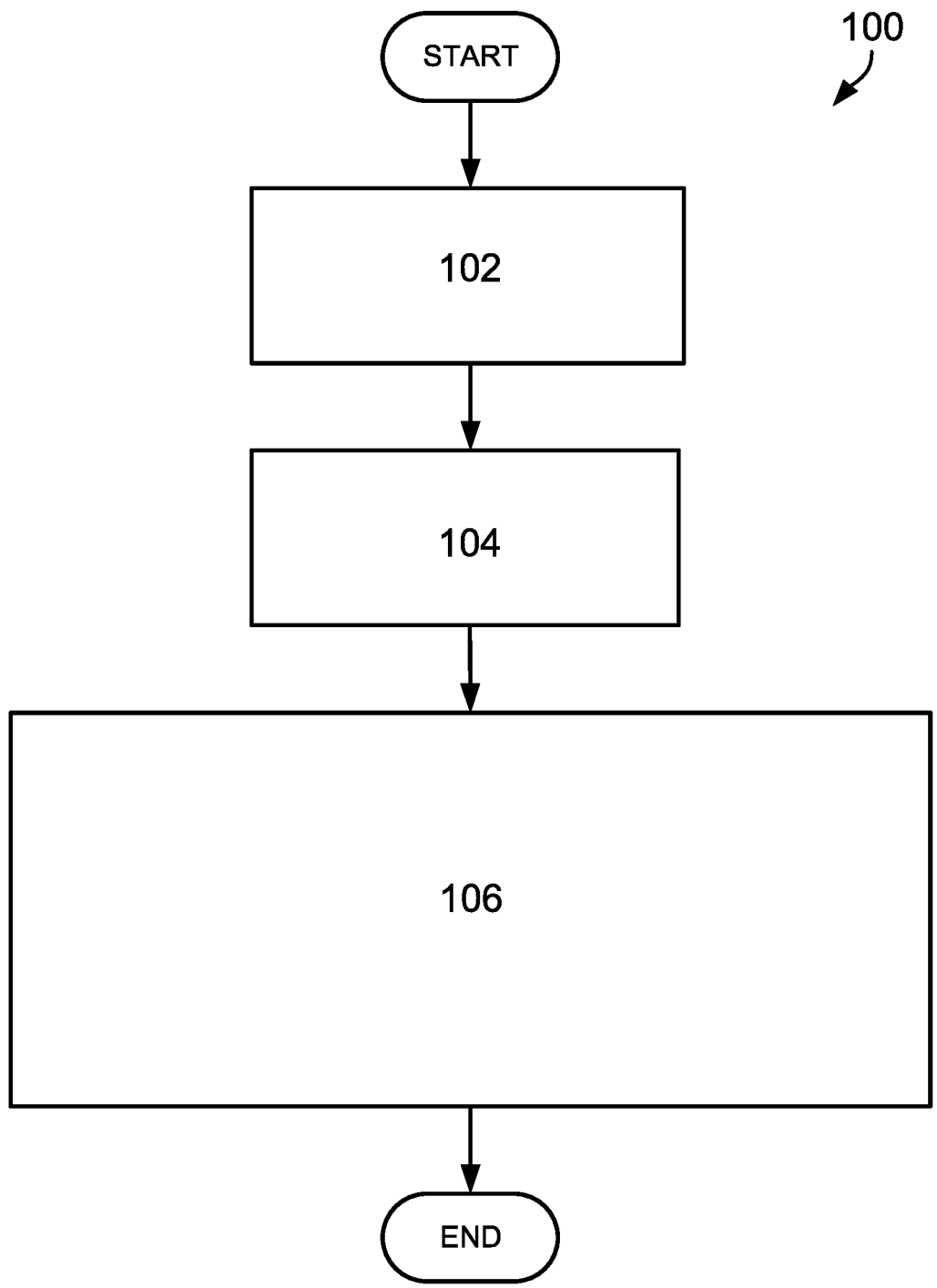
FIG. 8 is a flow diagram view of a method for generating a shear wave, via the vibration actuator, according to another embodiment of the present disclosure.

With reference now to FIG. 8, a method 100 for mechanically generating a shear wave via a vibration actuator according to another embodiment of the present disclosure will now be discussed. The method starts at Step 102 with providing a plurality of n rotational vibrators coupled to a housing in a geometric arrangement configured to enable generation of a vibration vector with desired directional behavior selected from a plurality of vibration vectors of different directional behaviors. The designation n is a number of at least three. In addition, each rotational vibrator comprises an independently controllable motor having a rotary drive shaft and an eccentric disk fixedly coupled to the rotary drive shaft in a plane perpendicular to an axis of the rotary drive shaft.

At Step 104, the method 100 includes detecting, via an accelerometer coupled to the housing, a vibration vector generated by at least two of the plurality of n rotational vibrators and generating an accelerometer output signal based on the detected vibration vector. The method then proceeds to Step 106, which includes selectively controlling, via a controller operatively coupled to each rotational vibrator, (i) a first set of two of the plurality of n rotational vibrators to rotate respective eccentric disks in a first coordinated manner based at least on the accelerometer output signal to produce a first shear wave vibration vector, and (ii) a second set of two of the plurality of n rotational vibrators to rotate respective eccentric disks in a second coordinated manner based at least on the accelerometer output signal to produce a second shear wave vibration vector. A directional behavior of the second shear wave vibration vector is different from a directional behavior of the first shear wave vibration vector.

In one embodiment, selectively controlling, via the controller, in Step 106 further comprises (i) determining a directional behavior of a resultant vibration vector based on (i)(a) the accelerometer output signal and (i)(b) the selectively controlled first set or second set of two of the plurality of n rotational vibrators to rotate respective eccentric disks, (ii) performing a comparison of a directional behavior of the resultant vibration vector to the desired directional behavior of the vibration vector, and (iii) adjusting the first or the second coordinated manner based on the comparison. In another embodiment, the first or second coordinated manner includes controlling the respective first or second set of rotational vibrators (i) with mirror symmetry of the respective eccentric disks to produce a vector vibration along a mid-plane direction between respective eccentric disks, and (ii) without mirror symmetry of the respective eccentric disks to produce a vector vibration deviation from the mid-plane direction.

According to another embodiment, the method 100 further comprises detecting, via a position sensor of a respective rotational vibrator, a radial orientation or rotational angle of the respective eccentric disk and generating a respective position signal based on the detected orientation or rotational angle. In addition, the step of controlling, via the controller, further comprises synchronously controlling, based on respective position signals, (i) the first set of two of the plurality of n rotational vibrators to rotate respective eccentric disks and produce the first vibration vector and (ii) the second set of two of the plurality of n rotational vibrators to rotate respective eccentric disks and produce the second vibration vector.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used as an additional feature for non-premium ultrasound systems, i.e. producing mechanically induced shear waves. In this manner, the embodiments of the present disclosure enable cost-effective elastography implementation on a greater number of ultrasound platforms/probes. The vibration actuator embodiments may also be useful in a number of applications which involve one or more of elastography, ultrasound imaging, tissue elastic properties, hepatology, and mechanical vibration shear waves. As mentioned earlier with respect to determining tissue elasticity, shear wave tissue vibration that aligns vibration motion with the direction of the ultrasound tracking beam is advantageous. To accomplish this alignment, it is beneficial to be able to alter the direction of shear wave motion during the determination of tissue elasticity. For example, one could decide to do multiple sequential measurements of tissue elasticity in a particular region but with a range of beam steering angles (e.g., with multiple bursts of tracking beams). Each of the beam steering angles would require a different direction of shear wave motion to optimize alignment. In another example, as the shear wave travels from the vibration actuator to the region of interest, its direction of traveling can change as it propagates through the tissue due to refraction effects caused by spatially varying tissue stiffness along the path of travel. Thus, the direction of vibration cannot be optimized deterministically ahead of time as it depends on tissue composition. Instead one can measure the direction of the shear wave in the region of interest, and adaptively alter the vibration pattern to optimize the vibration motion alignment. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A vibration actuator for mechanically generating a shear wave, comprising:
    a housing;
    a plurality of n rotational vibrators coupled to the housing in a geometric arrangement configured to enable generation of a vibration vector with desired directional behavior selected from a plurality of vibration vectors of different directional behaviors, wherein n is a number of at least three, wherein each rotational vibrator comprises an independently controllable motor having a drive shaft and an eccentric disk coupled to the drive shaft in a plane perpendicular to an axis of the drive shaft;
    an accelerometer coupled to the housing, wherein the accelerometer is arranged to detect a vibration vector generated by at least two of the plurality of n rotational vibrators and generate an accelerometer output signal based on the detected vibration vector; and
    a controller operatively coupled to each rotational vibrator for selectively controlling (i) a first set of two of the plurality of n rotational vibrators to rotate respective eccentric disks in a first coordinated manner based at least on the accelerometer output signal to produce a first vibration vector, and (ii) a second set of two of the plurality of n rotational vibrators to rotate respective eccentric disks in a second coordinated manner based at least on the accelerometer output signal to produce a second vibration vector, wherein a directional behavior of the second vibration vector is different from a directional behavior of the first vibration vector.

2. The vibration actuator according to claim 1, wherein the controller is further for selectively controlling (iii) a third set of two of the plurality of n rotational vibrators to rotate respective eccentric disks in a third coordinated manner based at least on the accelerometer output signal to produce a third vibration vector, wherein a directional behavior of the third vibration vector is different from the directional behavior of the second vibration vector and different from the directional behavior of the first vibration vector.

3. The vibration actuator according to claim 1, wherein the controller is further configured for (i) determining a directional behavior of a resultant vibration vector based on (i)(a) the accelerometer output signal and (i)(b) the selectively controlled first set or second set of two of the plurality of n rotational vibrators to rotate respective eccentric disks, (ii) performing a comparison of a directional behavior of the resultant vibration vector to the desired directional behavior of the vibration vector, and (iii) adjusting the first or the second coordinated manner based on the comparison.

4. The vibration actuator according to claim 1, wherein the first coordinated manner or the second coordinated manner includes rotating each respective eccentric disk of the respective first set or second set of two of the plurality of n rotational vibrators at a same rotary speed, but in opposite rotational directions.

5. The vibration actuator according to claim 1, wherein the first or second coordinated manner includes controlling the respective first or second set of rotational vibrators (i) with mirror symmetry of the respective eccentric disks to produce a vector vibration along a mid-plane direction between respective eccentric disks, and (ii) without mirror symmetry of the respective eccentric disks to produce a vector vibration deviation from the mid-plane direction.

6. The vibration actuator according to claim 1, wherein each eccentric disk of a respective motor of the respective first set or second set of two of the plurality of n rotational vibrators is arranged co-planar to one another within the respective first set or second set.

7. The vibration actuator according to claim 1, wherein each respective motor comprises a bi-axial motor, and further wherein each respective eccentric disk comprises a first eccentric disk coupled to a first end of a respective drive shaft and a second eccentric disk coupled to a second end of the respective drive shaft.

8. The vibration actuator according to claim 1, wherein each respective eccentric disk comprises a disk having an off-center weight, further wherein the respective off-center weight of respective eccentric disks of a respective first and second rotational vibrator are controlled, via the respective motor and the controller, to rotate in positions that are symmetrical to one another and to generate vibrations, wherein only vibrational components along a mid-plane between the respective first and second rotational vibrator remains, while vibrations in all other directions cancel each other.

9. The vibration actuator according to claim 1, wherein n comprises three, and wherein the geometric arrangement of three rotational vibrators comprises a triangular arrangement.

10. The vibration actuator according to claim 9, wherein the triangular arrangement comprises the three rotational vibrators having axes of their respective motor drive shafts located at apexes of a triangle, and further wherein the directional behavior of the first vibration vector (34) and the directional behavior of the second vibration vector (36) are selected from the group consisting of +120 degrees, 0 degrees and −120 degrees.

11. The vibration actuator according to claim 9, wherein the triangular arrangement is configured to enable achievement of multiple electronically selectable vibration orientations selected from the group consisting of (i)+15 degrees, 0 degrees and −15 degrees, (ii) +20 degrees, 0 degrees and −20 degrees, (iii) +30 degrees, 0 degrees and −30 degrees, and (iv) orientations in a range from +−10 to +−110 degrees.

12. The vibration actuator according to claim 1, wherein the geometric arrangement further includes the number of n rotational vibrators configured to enable generation of multiple electronically selectable vibration vectors in n*(n−1)/2 directions.

13. The vibration actuator according to claim 1, wherein each rotational vibrator further comprises a position sensor arranged to detect a radial orientation or rotational angle of the respective eccentric disk and generate a respective position signal, and wherein controlling via the controller further comprises synchronously controlling, based on respective position signals, (i) the first set of two of the plurality of n rotational vibrators to rotate respective eccentric disks and produce the first vibration vector and (ii) the second set of two of the plurality of n rotational vibrators to rotate respective eccentric disks and produce the second vibration vector.

14. The vibration actuator according to claim 13, wherein the position sensor comprises at least one selected from the group consisting of an optical position sensor and an inductive sensor, and wherein the position sensor further comprises one selected from the group consisting of (i) being integrated into a respective motor of a respective rotational vibrator of the plurality of n rotational vibrators and (ii) bring an additional component coupled to the respective motor.

15. An ultrasound probe for shear wave elastography, comprising:
 an ultrasound transducer array for generating ultrasound waves; and
 a vibration actuator according to claim 1 for generating mechanically induced shear waves; and
 an ultrasound probe controller operatively coupled to the ultrasound transducer array and the vibration actuator for implementing at least (i) a first mode of operation for generating and receiving ultrasound waves via the ultrasound transducer array and (ii) a second mode of operation for a combination of both (ii)(a) generating and receiving ultrasound waves and (ii)(b) generating mechanically induced shear waves via the ultrasound transducer array and the vibration actuator, respectively.

16. A system for shear wave elastography, comprising:
 an ultrasound probe according to claim 15;
 ultrasound system electronics operatively coupled to the ultrasound probe and arranged for obtaining ultrasound images in a first modality, and obtaining shear wave elastography images in a second modality; and
 a display coupled to the ultrasound system electronics for displaying the obtained ultrasound and shear wave elastography images.

17. A method for mechanically generating a shear wave via a vibration actuator, comprising:
 providing a plurality of n rotational vibrators coupled to a housing in a geometric arrangement configured to enable generation of a vibration vector with desired directional behavior selected from a plurality of vibration vectors of different directional behaviors, wherein n is a number of at least three, wherein each rotational vibrator comprises an independently controllable motor having a drive shaft and an eccentric disk coupled to the drive shaft in a plane perpendicular to an axis of the drive shaft;
 detecting, via an accelerometer coupled to the housing, a vibration vector generated by at least two of the plurality of n rotational vibrators and generating an accelerometer output signal based on the detected vibration vector; and
 selectively controlling, via a controller operatively coupled to each rotational vibrator, (i) a first set of two of the plurality of n rotational vibrators to rotate respective eccentric disks in a first coordinated manner based at least on the accelerometer output signal to produce a first vibration vector, and (ii) a second set of two of the plurality of n rotational vibrators to rotate respective eccentric disks in a second coordinated manner based at least on the accelerometer output signal to produce a second vibration vector, wherein a directional behavior of the second vibration vector is different from a directional behavior of the first vibration vector.

18. The method according to claim 17, wherein selectively controlling, via the controller, further comprises (i) determining a directional behavior of a resultant vibration vector based on (i)(a) the accelerometer output signal and (i)(b) the selectively controlled first set or second set of two of the plurality of n rotational vibrators to rotate respective eccentric disks, (ii) performing a comparison of a directional behavior of the resultant vibration vector to the desired directional behavior of the vibration vector, and (iii) adjusting the first or the second coordinated manner based on the comparison.

19. The method according to claim 17, wherein the first or second coordinated manner includes controlling the respective first or second set of rotational vibrators (i) with mirror symmetry of the respective eccentric disks to produce a vector vibration along a mid-plane direction between respective eccentric disks, and (ii) without mirror symmetry of the respective eccentric disks to produce a vector vibration deviation from the mid-plane direction.

20. The method according to claim 17, further comprising:

detecting, via a position sensor of a respective rotational vibrator, a radial orientation or rotational angle of the respective eccentric disk and generating a respective position signal based on the detected orientation or rotational angle, wherein controlling, via the controller, further comprises synchronously controlling, based on respective position signals, (i) the first set of two of the plurality of n rotational vibrators to rotate respective eccentric disks and produce the first vibration vector and (ii) the second set of two of the plurality of n rotational vibrators to rotate respective eccentric disks and produce the second vibration vector.

\* \* \* \* \*